United States Patent [19]
Lee et al.

[11] Patent Number: 5,807,827
[45] Date of Patent: Sep. 15, 1998

[54] DES-TYR DYNORPHIN ANALOGUES

[75] Inventors: Nancy M. Lee; Horace H. Loh, both of San Francisco, Calif.; Akira E. Takemori, Edina, Minn.

[73] Assignee: Des-Tyr Dynorphin Partnership, San Francisco, Calif.

[21] Appl. No.: 856,053

[22] Filed: May 14, 1997

Related U.S. Application Data

[63] Continuation of Ser. No. 581,479, Dec. 20, 1995, abandoned, which is a continuation of Ser. No. 127,132, Sep. 27, 1993, abandoned, which is a continuation-in-part of Ser. No. 897,920, Jun. 12, 1992, abandoned.

[51] Int. Cl.$^6$ .......................... A61K 38/00; A61K 38/02; C07K 5/00; C07K 7/00
[52] U.S. Cl. .................................................. 514/14; 514/13
[58] Field of Search ..................................... 530/326, 324, 530/328, 329; 514/13, 14, 15, 16, 17

[56] References Cited

U.S. PATENT DOCUMENTS

| | | | |
|---|---|---|---|
| 4,361,553 | 11/1982 | Loh et al. | 424/177 |
| 4,396,606 | 8/1983 | Goldstein . | |
| 4,462,941 | 7/1984 | Lee et al. . | |
| 4,481,191 | 11/1984 | Wei et al. . | |
| 4,518,711 | 5/1985 | Hruby et al. . | |
| 4,684,624 | 8/1987 | Hosobuchi et al. . | |

FOREIGN PATENT DOCUMENTS

WO9606626  3/1996  WIPO .

OTHER PUBLICATIONS

Bakshi and Faden, "Competitive and Non-Competitive NMDA Antagonists Limit Dynorphin A–Induced Rat Hindlimb Paralysis," *Brain Research*, 507, pp. 1–5 (1990).

Rochford et al., "Intrathecal Administration of Dynoprhin A and Its Fragments Increase Heart Rate and Arterial Pressure in the Urethane Anesthetized Rat . . . " *Brain Research*, 565, pp. 67–77 (1991).

Codd et al., "A Non–Opioid Pattern Characterizes Inhibition of Growth Hormone Releasing Peptide Binding By Dynorphin–Rleated Peptides," *Neuropeptides*, 15, pp. 133–137 (1990).

Meyer, Merle E., "Intrastriatal Injections of Dynorphin A Fragments Potentiate the Dorsal Immobility Response in Rats," *Pharmacology Biochemistry and Behavior*, 44, pp. 329–332 (1993).

Takemori et al., "Suppression by Dynorphin A and [Des–Tyr$^1$] Dynorphin A Peptides of the Expression of Opiate Withdrawal & Tolerance in Morphine–Dependent Mice," *J. of Pharmac. & Exp. Ther.*, 266:1, pp. 121–124 (1993).

Smith and Lee, "Pharmacology of Dynorphin," *Ann. Rev. Pharmacol. Toxicol.*, 28, (1988) pp.123–140.

Sibinga and Goldstein, "Opioid Peptides and Opioid Receptors in Cells of the Immune System," *Ann. Rev. Immunol.*, 6, (1988) pp. 218–249.

Roy et al., "Chronic Morphine Treatment Selectively Suppresses Macrophage Colony Formation in Bone Marrow," *Eur. J. of Pharm.*, 195 (1991) pp. 359–363.

Roy et al., "Dynorphyin Blocks Opioid Inhibition of Macrophage–Colony Stimulating Factor–Induced Proliferation of Bone Marrow Cells," *Eur. J. of Pharm.*, 202 (1991) pp. 355–359.

Xie et al., "Expression Cloning of cDNA Encoding a Seven–Helix Receptor from Human Placenta with Affinity for Opioid Ligands," *Proc. Natl. Acad. Sci. USA* 89 (1992), pp. 4124–4128.

Schiller et al., "Dermorphin Analogues Carrying an Increased Positive Net Charge in Their Message Domain Display Extremely High $\mu$ Opioid Receptor Selectivity", *J. of Med. Chem.*, 32 (1989) pp. 698–703.

D'Amour et al., "A Method for Determining Loss of Pain Sensation," *J. Pharmac. Exp. Ther.*, 72 (1941) pp. 74–79.

Tulunay et al., "The Increased Efficacy of Narcotic Antagonists Induced by Various Narcotic Analegsics," *J. Pharmac. Exp. Ther.*, 190 (1974) pp. 395–400.

Way et al., "Simultaneous Quantitative Assessment of Morphine Tolerance and Physical Dependence," *J. Pharmac. Exp. Ther.*, 167 (1969) pp. 1–8.

Litchfield et al., "A Simplfied Method of Evaluating Dose–Effect Experiments," *J. Pharmac. Exp. Ther.*, 96 (1949) pp. 99–113.

Long et al., Europ J. Pharmacology., vol. 153, pp. 45–54, 1988.

Smith et al., Ann. Rev. Pharmacol. Toxicol., vol. 28, pp. 123–140, 1988.

Smith et al, *Ann. Rev. Pharmacol. Toxicol.*, vol. 28, 1988, pp. 123–140.

Walker et al., Science, vol. 218, 10 Dec. 1982, pp. 1136–1138.

Faden et al., *Br. J. Pharmac.*, vol. 81, 1984, pp. 271–276.

Walker et al., "Nonopiate Effects of Dynorphin and Des–Tyr–Dynorphin," *Science*, 218 (1982), pp.1136–1138.

Long et al., "Intrathecal Dynorphin A(1–13) and Dynorphin A(3–13) Reduce Rat Spinal Cord Blood Flow by non–opioid Mechanims," *Brain Res.*, 436(1987), pp. 374–379.

*Primary Examiner*—Avis M. Davenport
*Attorney, Agent, or Firm*—Majestic, Parsons, Siebert & Hsue

[57] ABSTRACT

Novel peptides of the invention are dynorphin analogues and have similar activity to endogenous dynorphin, but are des-Tyr or des-Tyr-Gly with respect to endogenous dynorphin and have at least seven amino acid residues. The novel peptides have therapeutic uses, such as administration to a host tolerant to a narcotic analgesic in order to potentiate activity of the narcotic analgesic and/or to block withdrawal symptoms.

5 Claims, No Drawings

DES-TYR DYNORPHIN ANALOGUES

This is a continuation of application Ser. No. 08/581,479, filed Dec. 20, 1995 and now abandoned, which was a continuation of application Ser. No. 08/127,132, filed Sep. 27, 1993 and now abandoned, which was a continuation-in-part of application Ser. No. 07/897,920, filed Jun. 12, 1992 and now abandoned.

FIELD OF THE INVENTION

The present invention generally relates to dynorphin analogues, and more particularly to novel dynorphin analogues that can be used with narcotic analgesics, such as opiate alkaloids. This invention was made with government support under Grant No. NIDA-02643 awarded by the National Institutes of Health. The Government has certain rights in this invention.

BACKGROUND OF THE INVENTION

The endogenous opioids exist in multiple forms in the central nervous system and include the dynorphins, which are a series of peptides derived from the precursor prodynorphin (proenkephalin B). The first of the dynorphins to be isolated was the 17 amino acid peptide having the structure shown (and designated SEQ ID NO:1), sometimes also referred to as "dynorphin A (1–17)":

Tyr-Gly-Gly-Phe-Leu-Arg-Arg-Ile-Arg-Pro-Lys-Leu-Lys-Trp-Asp-Asn-Gln (SEQ ID NO:1)

Unlike either the enkephalins or the endorphins, many of the dynorphins interact with high affinity with all three major opioid receptor types ($\mu$, $\delta$, and $\kappa$). The dynorphins are also nearly unique among endogenous opioids in that they are not analgesic in the brain, although they may be in the spinal cord.

Smith and Lee have recently reviewed the pharmacology of dynorphin in *Ann. Rev. Pharmacol. Toxicol.*, 28, pp. 123–140 (1988). They note a growing body of evidence has indicated that endogenous opioids are closely connected with function of the immune system. The reviewers, however, state that dynorphin had not been tested in any of the studies reviewed, except for one study concerning mononuclear cell chemotaxis. However, the reviewers note that dynorphin has been implicated in tumor formation.

Several U.S. patents have suggested uses of dynorphin. U.S. Pat. No. 4,361,553, issued Nov. 30, 1982, inventors Loh and Lee, set out the sequence of the first thirteen peptides for the naturally occurring dynorphin (containing seventeen amino acids), which had been discovered to have potent agonist properties in guinea pig ileum and mouse vas deferens. This patent describes the discovery that dynorphin, and particularly dynorphin A (1–13) has an opposite effect in hosts tolerant to narcotic analgesic than the effect which has been observed in naive animals (an inhibition of morphine or β-endorphin-induced analgesia). Thus, dynorphin A (1–13) potentiates the analgesic effect in tolerant hosts. Dynorphin was found useful in conjunction with a narcotic analgesic in order to reduce the amount of narcotic analgesic administered per dose.

U.S. Pat. No. 4,396,606, issued Aug. 2, 1983, inventor Goldstein, describes isolation of a compound referred to as "dynorphin" (sometimes hereinafter called "dynorphin (1–13)") with the structure:

Tyr-Gly-Gly-Phe-Leu-Arg-Arg-Ile-Arg-Pro-Lys-Leu-Lys (SEQ ID NO:2)

This compound was found to be substantially more active than the enkephalins and β-endorphin in a guinea pig ileum test, and compositions containing the compound were suggested to be analgesic.

U.S. Pat. No. 4,462,941, issued Jul. 31, 1984, inventors Lee et al., describes dynorphin amide analogs with the first seven amino acids as in SEQ ID NO:1 and SEQ ID NO:2, but with the next several amino acids as:

$AA^8$-$AA^9$-$AA^{10}$ wherein $AA^8$ is isoleucine, leucine, or lysine, $AA^9$ is arginine or proline, $AA^{10}$ is proline, and a carbonyl carbon at the $AA^{10}$ terminus is amidated. These dynorphin (1–10) amide analogs do not have significant analgesic activity (unless given in huge doses where they tend to produce convulsions), but they differ from the SEQ ID NO:2, dynorphin (1–13) by neither potentiating nor antagonizing morphine in naive animals. In tolerant animals, on the other hand, the dynorphin (1–10) amide analogs appear to be a more potent and selective analog than dynorphin (1–13). SEQ ID NO:3 represents a particular one of these dynorphin (1–10) amide analogs (where the C-terminal Pro is amidated):

Tyr-Gly-Gly-Phe-Leu-Arg-Arg-Ile-Arg-Pro (SEQ ID NO:3)

U.S. Pat. No. 4,481,191, issued Nov. 6, 1984, inventors Wei et al., describe a method for treating high blood pressure and disturbances of cardiac function by administrating dynorphin-related opioid peptides, such as the SEQ ID NO:2 and SEQ ID NO:3 peptides. It appears that endogenous opioid peptides condition the sensitivity of the peripheral nerves to stimuli that affect heart rate and blood pressure. Thus, circulating opioid peptides, under normal conditions, are operating to control the sensitivity of these peripheral sites of the autonomic nervous system to such endogenous substances. Use of the dynorphin-related peptides in treating high blood pressure appears to modify the autonomic nervous system so as to amplify and maintain the intensity of endogenous opioid peptides. A mode of action may be by increasing the sensitivity of visceral afferent receptors.

Enkephalin analogues that are conformationally constrained by a cyclic structure (such as with a disulfide bridge) are described by U.S. Pat. No. 4,518,711, issued May 21, 1985, inventors Hruby et al. These compounds are said to have increased rigidity and increased delta receptor specificity if the half-cysteine in the 2 position is replaced by half-penicillamine (β,β-dimethyl half-cysteine). Subsequently, dynorphin analogues have become known that have cysteine replacements at the amino acid residue 5 (usually leucine) and at the amino acid residue 11 (usually lysine). The amino acid residue 8 (usually an isoleucine) and the amino acid residue 13 (usually a lysine) have similarly been replaced by cysteines in a bridged relationship. The bridges, or cyclic structures, appear to assist in stabilizing the dynorphin analogues against in vivo degradations.

U.S. Pat. No. 4,684,624, issued Aug. 4, 1987, inventors Hosobuchi et al., describe the use of dynorphin-related peptides, in the acid or amidated form, to treat patients suffering from cerebral ischemia. The administration of these opioid peptides to patients suffering from acute focal cerebral ischemia has been found useful in prolonging survival, and appears useful in partially reversing neurologic deficits resulting from cerebral ischemia.

Investigators have recently begun attempts to link immuno regulation to neural opioid systems. It has become increasingly clear there are a number of opioid effects on cells of the immune system, but the mechanisms remain obscure. The authors of a recent review have concluded that the significance of opioids in immune system function remain a matter for speculation. Sibinga and Goldstein, *Ann. Rev. Immunol.*, 6, pp. 219–249 (1988).

In 1991, Roy et al. reported that mice having been treated with chronic morphine were immuno-suppressed, whereas use of either SEQ ID NO:2 or SEQ ID NO:3 was found to block the opioid inhibition of macrophage-colony stimulating factor of morphine in a dose-dependent manner. *Eur. J. of Pharm.*, 195, 359–363 (1991); 202, 355–359 (1991).

SUMMARY OF THE INVENTION

In one aspect of the present invention, novel peptides are described that have at least seven amino acid residues, are analogues of dynorphin, but are des-Tyr with respect to the endogenous dynorphin. These novel peptides may be formulated in a pharmaceutically acceptable solution or with a pharmaceutically acceptable carrier, and are usefully administered to a host tolerant to a narcotic analgesic in order to potentiate activity of the narcotic analgesic and/or to block withdrawal symptoms. Additional uses include the reversal of at least some neurologic deficit in treating cerebral and spinal ischemia, in inhibiting respiratory depression or gastroenteric spasms produced by narcotic analgesics to a naive host, as an adjunct for anti-inflammatory medication, and in blocking narcotic induced immune impairment in a host whose immune system has been impaired by a narcotic analgesic.

Thus, novel peptides of the invention generally have similar activity to endogenous dynorphin (SEQ ID NO:1), to dynorphin with thirteen amino acids (SEQ ID NO:2), and to dynorphin in amide form with ten amino acids (SEQ ID NO:3); however, it is surprising that the novel compounds, which are des-Tyr with respect to such previously known dynorphin compounds, exhibit similar biological activity because the N-terminal tyrosine has been considered a substantially universal requirement for recognition of opioid peptides by opioid receptors. For example, researchers in the field seeking to clone cDNA encoding an opioid receptor have recently noted that the des-Tyr Dyn A (1–13) did not compete at all in assays with various ligands (pp. 4126 and 4127–4128), and recited the conventional wisdom concerning the "necessity" of the N-terminal Tyr. Xie, Miyajima, and Goldstein, *Proc. Natl. Acad. Sci. USA*, 89, pp. 4124–4128 (1992).

In the therapeutic uses of this invention that include administration to a host tolerant to a narcotic analgesic, lower doses of the narcotic analgesic, for example an opiate alkaloid such as morphine, may be used for patients requiring chronic treatment with narcotics to ease pain, such as terminal cancer patients, or lower doses of a narcotic such as methadone may be used in treating narcotics addicts. As a consequence, the various, known side effects, such as respiratory depression and constipation, which result from chronic treatment with high doses of narcotics, can be lessened by practice of the invention.

DETAILED DESCRIPTION OF THE EMBODIMENT

In the parent application of which this is a continuation-in-part, we had thought that at least six amino acids would be necessary for the various desirable therapeutic applications herein described, where the amino acids were preferably in the sequence: Gly-Phe-Leu-Arg-Arg-Ile (SEQ ID NO:22). However, we have now found that the minimal amino acid sequence required has seven amino acids, as will be hereinafter further described.

In one aspect of this invention, novel peptides can be viewed as having amino acid residues analogous to endogenous dynorphin (SEQ ID NO:1), but where the novel peptides are des-Tyr, as shown by SEQ ID NOS:4–12:

Gly-Gly-Phe-Leu-Arg-Arg-Ile-Arg-Pro-Lys-Leu-Lys-Trp-Asp-Asn (SEQ ID NO:4);
Gly-Gly-Phe-Leu-Arg-Arg-Ile-Arg-Pro-Lys-Leu-Lys-Trp-Asp (SEQ ID NO:5);
Gly-Gly-Phe-Leu-Arg-Arg-Ile-Arg-Pro-Lys-Leu-Lys-Trp (SEQ ID NO:6);
Gly-Gly-Phe-Leu-Arg-Arg-Ile-Arg-Pro-Lys-Leu-Lys (SEQ ID NO:7);
Gly-Gly-Phe-Leu-Arg-Arg-Ile-Arg-Pro-Lys-Leu (SEQ ID NO:8);
Gly-Gly-Phe-Leu-Arg-Arg-Ile-Arg-Pro-Lys (SEQ ID NO:9);
Gly-Gly-Phe-Leu-Arg-Arg-Ile-Arg-Pro (SEQ ID NO:10);
Gly-Gly-Phe-Leu-Arg-Arg-Ile-Arg (SEQ ID NO:11); and,
Gly-Gly-Phe-Leu-Arg-Arg-Ile (SEQ ID NO:12).

In any of the novel SEQ ID NOS:4–12, any one or two of the residues may be replaced with the same or a different amino acid residue in the D-configuration (to increase in vivo stability), such as where the N-terminal Gly is replaced by D-Ala, or a modification for conformational stability or rigidity may be made, such as where a plurality of the specified amino acid residue are replaced by moieties capable of forming a cyclic structure, or bridge (e.g., the disulfide bridge).

Novel peptides for this invention can also be viewed as des-Tyr-Gly, as shown by SEQ ID NOS:13–21, which can similarly be modified to increase in vivo stability and conformational stability as already described for SEQ ID NOS:4–12:

Gly-Phe-Leu-Arg-Arg-Ile-Arg-Pro-Lys-Leu-Lys-Trp-Asp-Asn-Gln (SEQ ID NO:13);
Gly-Phe-Leu-Arg-Arg-Ile-Arg-Pro-Lys-Leu-Lys-Trp-Asp-Asn (SEQ ID NO:14);
Gly-Phe-Leu-Arg-Arg-Ile-Arg-Pro-Lys-Leu-Lys-Trp-Asp (SEQ ID NO:15);
Gly-Phe-Leu-Arg-Arg-Ile-Arg-Pro-Lys-Leu-Lys-Trp (SEQ ID NO:16);
Gly-Phe-Leu-Arg-Arg-Ile-Arg-Pro-Lys-Leu-Lys (SEQ ID NO:17);
Gly-Phe-Leu-Arg-Arg-Ile-Arg-Pro-Lys-Leu (SEQ ID NO:18);
Gly-Phe-Leu-Arg-Arg-Ile-Arg-Pro-Lys (SEQ ID NO:19);
Gly-Phe-Leu-Arg-Arg-Ile-Arg-Pro (SEQ ID NO:20); and,
Gly-Phe-Leu-Arg-Arg-Ile-Arg (SEQ ID NO:21).

The novel peptides illustrated by SEQ ID NOS:1–21 can be in the acid or amide form at the C-terminus. Further, the usual isoleucine amino acid residue in SEQ ID NOS:4–21 can be replaced with leucine or lysine, and the usual arginine at position 8 of SEQ ID NOS:4–11 and at position 7 of SEQ ID NOS:13–21 can be replaced with proline.

One model potentially useful for choosing particular modifications is based upon a prediction that receptor selectivity of opioid peptides is governed by their net charge and/or amphiphilic moment, in addition to the structural and conformational requirements of a particular opioid receptor type ($\mu$, $\delta$, and $\kappa$). This model predicts that opioid peptides with a net positive charge would show $\mu$-receptor preference while neutral and negatively charged opioid peptides would preferentially interact with the $\delta$-receptor, and the model has been used, for example, in designing small peptides by Schiller et al., *J. of Ned. Chem.*, 32, pp. 698–703 (1989).

Novel peptides of the invention are preferably formulated in a pharmaceutically acceptable solution or with a pharmaceutically acceptable carrier, and then are administered in conjunction with a narcotic analgesic.

Depending upon the mode of administration, the peptide may be formulated with a wide variety of physiologically acceptable carriers, such as aqueous saline and phosphate buffered saline, and may include physiologically acceptable excipients, such as glucose, mannitol, or the like.

In addition to use of the novel peptides in the therapeutic applications described more fully below, we have surprisingly discovered that the dynorphin (1–17), also known as SEQ ID NO:1, but when des-Tyr (and thus described as SEQ ID NO:23), retains sufficient of the desired activity in conjunction with narcotic analgesics to be useful.

The present invention is useful with substantially all narcotic analgesics, and more preferably the opiate alkaloids and opioid peptides (both synthetic and natural). For example, the invention is useful with the various alkaloids of opium such as morphine, morphine salts (such as morphine hydrobromide, morphine hydrochloride, morphine muscate, morphine oleate, morphine N-oxide, and morphine sulfate), and morphine analogs such as normorphine, diacetyldihydromorphine, diacetylmorphine hydrochloride, codeine, and diacetylmorphine (heroin). Other widely used narcotic analgesics with which the present invention may be used include alphaprodine, methadone, meperidine, levorphanol, propoxyphene, fentanyl and its analogues, oxymorphone, anileridine, dilaudid, and metopon. Uses can be extended to the peptide analgesics, such as enkephalins and β-endorphin analogs.

As is well known, continued use of these narcotic analgesics leads to habituation or addiction, and use of one leads to cross-tolerance for the others. However, despite their abuse potential, these narcotic analgesics have therapeutic uses, for example with patients requiring chronic treatment to ease pain.

Even in such therapeutic uses, though, patients develop increasing tolerances to these narcotic analgesics, so that increasingly potent doses are required to achieve relief from pain. Undesirable side effects then tend to develop to the large, chronic doses of the narcotic analgesics.

The agonistic actions and dependence-producing properties of narcotic analgesics can be, and are, studied in various mammalian species besides humans, since practical and governmental considerations frequently require that studies be first done in small rodents and/or monkeys before the analgesic properties of pharmaceuticals are tested with humans. To the present, however, all drugs that have morphine-like properties in mammals other than humans have been found to be morphine-like in humans, and a variety of analgesic assays have been developed with animals which have gained widespread acceptance for predicting properties in humans.

The present invention includes administering a dose of one of the analogues SEQ ID NOS:4–21 and 23, or a modified version thereof as has been described, to a host in conjunction with administering a dose of a narcotic analgesic, wherein the administration is within at least about 30 minutes of the narcotic analgesic dose. Preferably the administering is by administering a single, admixed dose where the narcotic analgesic, is morphine, a morphine analogue, or a morphine salt, or other peptide analgesics.

Where administering of narcotic analgesic is morphine and is to a naive patient, a normal dosage is on the order of about 5 mg i.v., assuming a body weight of about 70 kg. It is believed a suitable dose of the dynorphin analogue, administered in conjunction with the analgesic, is from about 30–1500 µg per kg body weight. Although the dynorphin analogue does not potentiate the narcotic analgesic in an initially naive host, as the patient continues in an extended treatment with narcotics to ease pain, the amount of narcotic required to produce a sufficient level of analgesia over the treatment period will be less than without use of dynorphin analogue in conjunction with the narcotic. As a consequence, the various undesirable side effects of repeated, high doses of narcotics, can be lessened.

The dosage in tolerant patients may be determined as follows. A first, or sufficient, dose of the narcotic analgesic is determined which would be sufficient to produce analgesia in the host. However, instead of administering the sufficient dose, a predetermined dose of the narcotic analgesic is administered. This predetermined, or second, dose includes less of the narcotic analgesic than would be sufficient to produce analgesia in the host. The actually administered dose of narcotic analgesic is supplemented with dynorphin analogue. The supplementation is preferably sufficient to produce a level of analgesia in the host which is substantially equivalent to the level of analgesia were solely the narcotic analgesic to have been administered. As may be understood, the first or sufficient dose, the lower, second dose, and the supplementing dose will vary depending upon the patient's particular level of tolerance to the narcotic analgesic, and will normally be determined by the treatment physician.

Another therapeutic method of use is in treating addicts to substantially block withdrawal symptoms.

Presently, many addicts are placed upon a methadone (usually methadone hydrochloride) maintenance program. In conjunction with the administration of methadone, another drug, such as clonidine, is administered in conjunction therewith. However, as is well known, methadone is itself addictive, and clonidine is believed to simply mask withdrawal symptoms. As a consequence, patients on such programs are not actually being "cured" of their narcotic addiction.

By contrast, dynorphin analogues block the withdrawal symptoms of morphine addicted hosts, yet are at least 100 times less addictive than morphine. Accordingly, the administrating of the present invention may be used to assist in blocking withdrawal symptoms in therapeutic treatments of narcotic addicts being treated for addiction.

Thus, it is believed that administering a dose of dynorphin analogue to a host tolerant to narcotic analgesics will provide a significantly more desirable treatment in treating narcotic addiction.

Novel peptides of the invention can further be used partially to reverse neurologic deficits in cerebral ischemia. It is believed that factors affecting response to therapy for cerebral ischemia in accordance with the present invention include the dosage, the route of administration, and duration of therapy. However, blood pressure does not appear to be a factor affecting response to therapy for cerebral ischemia in accordance with the present invention.

In treating patients suffering from acute focal cerebral ischemia in accordance with the present invention, therapy is initiated by administering a dose of the dynorphin analogue and then preferably continued by administering subsequent doses.

The initial dose may be from about 1.0 µg/kg of patient's weight to about 10 mg/kg of patient's weight, more preferably about 100 µg/kg of patient';s weight, and can be delivered by various means known to the art, such as by intravenous injection ("I.V."). Subsequent doses may also be delivered by various means known to the art, such as by injections or through topical applications in conjunction with a drug carrier, such as dimethyl sulfoxide. However, it is preferred that the subsequent doses be delivered substantially continuously for as long as the patient is in a life threatening situation, or until the patient's condition stabilizes, and be at a rate between about 0.01 μg/hr to about 100 μg/hr. For example, continuous infusion may be by use of an implanted mini-pump, or by I.V. When the patient's condition stabilizes, then the doses may be gradually reduced, or titrated.

Aspects of the invention will now be illustrated by the following examples.

EXAMPLE 1

Methods and Materials

Analgesia was measured by the tail-flick method of D'Amour and Smith, *J. Pharmac. Exp. Ther.*, 72, pp. 74–79 (1941), incorporated herein by reference, as modified by Tulunay and Takemori, *J. Pharmac. Exp. Ther.*, 190, pp. 395–400 (1974), incorporated herein by reference. For $ED_{50}$ (e.g., effective does for 50% of the test group) determinations, the animals' responses were made quantal by establishing an endpoint which represented a significant increase in reaction time. The endpoint was an increase in reaction time of an individual animal of greater than 3 SD (e.g., standard deviation) of the control mean reaction time for all animals used in the assay. The usual control mean reaction time was 3.1±0.05 sec. Nonresponding animals were removed from the heat stimulus when reaction time exceeded 10 sec. to avoid tail damage.

Drugs were injected 30 minutes prior to testing, unless otherwise indicated. Morphine was injected subcutaneously (s.c.) whereas the peptides were injected (i.v.) in 4 ml saline.

Morphine tolerance was established by implanting morphine pellets, 75 mg base, subcutaneously by the method of Way et al., *J. Pharmac. Exp. Ther.*, 167, pp. 1–8 (1969), incorporated herein by reference. The drug used was morphine sulfate (Mallinckrodt Chemical Works, St. Louis, Mo.). The $ED_{50}$ values, their 95% confidence limits and significance of the potency ratio between two $ED_{50}$ values were determined by the method of Litchfield and Wilcoxon, *J. Pharmac. Exp. Ther.*, 96, 99–113 (1949), incorporated herein by reference.

Procedure for Table 1 Data

The morphine tolerant (addicted) animals had pellets implanted for three days. The animals were then challenged with naloxone doses (while the morphine pellet remained in place). The naloxone places the animals into a state of narcotic withdrawal and the animal exhibits withdrawal symptoms because naloxone is an antagonist of morphine. Table 1 summarizes the data for the control animals and for groups of animals treated with three different peptides. Each peptide was in a dose of 5 μmol/kg i.v. before administration of the naloxone.

TABLE 1

| Peptide Administered | Naloxone $ED_{50}$ (μmol/kg) | Potency Ratio |
|---|---|---|
| (control) | 79 (59–107) | — |
| Dyn (2–17) SEQ ID NO:23 | 289 (218–378) | 3.7 (2.5–5.4) |
| [Cys$^5$-Cys$^{11}$] Dyn (1–11) NH$_2$ | 208 (151–279) | 2.6 (1.7–3.9) |
| Dyn (3–13) SEQ ID NO:17 | 154 (102–249) | 2.0 (1.2–3.6) |

As is seen by the data of Table 1, the control animals had an $ED_{50}$ of 79 μmol/kg, which was the base line value. However, when any of the three peptides shown in Table 1 was administered five minutes before administration of the naloxone, then much more naloxone was needed to precipitate the animal into a state of narcotic withdrawal. This means that each of the three peptides shown in Table 1 caused the addicted animal to be not as dependent on morphine as it would be without such pretreatment.

Of the three peptides summarized in Table 1, the dynorphin (3–13), SEQ ID NO:17 is also a novel compound. Although this novel compound is des-Tyr-Gly, it has a potency ratio of 2. That is, addicted animals that were pretreated with this novel peptide before receiving the narcotic antagonist were only half as dependent on morphine as addicted animals which were not so pretreated. Additionally, the cyclic dynorphin amide compound used (where the normal leucine at the 5 position and the normal lysine at the 11 position had been replaced by cysteines, whose disulfide bridge provides conformational stability) had a potency ratio of 2.6, while the des-Tyr compound surprisingly had a potency ratio of 3.7.

EXAMPLE 2

Materials and Methods

The animals and test procedures used were analogous to those described in Example 1.

Protocol for Table 2

The antinociceptive activity ("pain killing") of morphine was tested in morphine tolerant (that is, addicted) mice, as well as in naive, unaddicted (that is, normal) animals. Two base lines were thus established for the two different control animals.

TABLE 2

| Peptide Administered | Morphine $ED_{50}$ (μmol/kg s.c.) | Tolerance Index |
|---|---|---|
| (control[1] -- naive, un- addicted animals) | 6.5 (5.0–8.9) | — |
| (control[2] -- addicted animals) | 55.6 (42.6–73.5) | 8.5 (5.7–12._) |
| (addicted animals) Dyn (2–17) SEQ ID NO:23 | 32.2 (26.7–40.0) | 4.7 (3.5–6.2) |

As is seen from the data of Table 2, the first control (unaddicted) animals had a morphine $ED_{50}$ of 6.5. This means that when the naive animals were administered 6.5 μmol/kg s.c. morphine before the tail flick test, then half of those animals felt no pain. By contrast, the second control group, which were morphine addicted animals, required an amount of morphine increased by a factor of 8.5 in order for half of the animals to feel no pain. However, the similarly addicted animals, when pretreated with the des-Tyr compound (at 2.5 μmol/kg i.v. 5 minutes before testing) had a significantly decreased amount of morphine necessary for the pain relief.

EXAMPLE 3

The animals and test procedures used were analogous to those described in Example 1. We studied various short fragments of dyn A to determine the minimal amino acid sequence that was necessary to retain the ability to suppress morphine withdrawal. Dyn A-(2–8), dyn A-(2–11), and dyn A-(2–14) (SEQ ID NOS: 12, 9 and 6) all inhibited withdrawal jumping with potencies slightly less than that of dyn A-(2–17) (SEQ ID NO:23). However, dyn A-(3–8) (SEQ ID NO:22) did not retain the anti-jumping property. Animals that were treated with dyn A-(3–13) were lethargic and exhibited partial paralysis of their hind quarters.

We conclude that of the des-Tyr dynorphin fragments, the minimal amino acid sequence required to suppress naloxone-induced withdrawal is the seven amino acid residue fragment dyn A-(2–8) (SEQ ID NO:21) rather than the six amino acid residue fragment dyn A-(3–8) (SEQ ID NO:22) as we had earlier believed.

It is to be understood that while the invention has been described above in conjunction with preferred specific embodiments, the description and examples are intended to illustrate and not limit the scope of the invention, which is defined by the scope of the appended claims.

---

It is claimed:

1. A therapeutic method for treating a patient tolerant to a narcotic analgesic comprising:

administering a dose of a dynorphin analogue in an amount effective to block narcotic analgesic withdrawal symptoms, the dynorphin analogue administered being a dynorphin analogue that is des-Tyr or des-Tyr-Gly at the N-terminus and has at least seven amino acid residues.

2. The therapeutic method as in claim 1 wherein the dynorphin analogue is administered in a pharmaceutically acceptable solution.

3. The therapeutic method as in claim 1 wherein the dynorphin analogue is amidated at the C-terminus.

4. The therapeutic method as in claim 1 wherein the dynorphin analogue has D-alanine as the N-terminal amino acid residue.

5. A therapeutic method for treating a patient tolerant to a narcotic analgesic comprising:

administering a dose of a dynorphin analogue in an amount effective to potentiate a narcotic analgesic when administered in conjunction therewith, the dynorphin analogue administered being a dynorphin analogue that is des-Tyr or des-Tyr-Gly at the N-terminus and has at least seven amino acid residues.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: porcine ( x i ) SEQUENCE DESCRIPTION: SEQ ID NO:1:

```
Tyr  Gly  Gly  Phe  Leu  Arg  Arg  Ile  Arg  Pro  Lys  Leu  Lys  Trp  Asp  Asn
1                  5                        10                       15
Gln
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: porcine ( x i ) SEQUENCE DESCRIPTION: SEQ ID NO:2:

```
Tyr  Gly  Gly  Phe  Leu  Arg  Arg  Ile  Arg  Pro  Lys  Leu  Lys
1                  5                        10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:

( A ) ORGANISM: porcine ( x i ) SEQUENCE DESCRIPTION: SEQ ID NO:3:

```
Tyr Gly Gly Phe Leu Arg Arg Ile Arg Pro
1               5                   10
```

( 2 ) INFORMATION FOR SEQ ID NO:4:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: porcine ( x i ) SEQUENCE DESCRIPTION: SEQ ID NO:4:

```
Gly Gly Phe Leu Arg Arg Ile Arg Pro Lys Leu Lys Trp Asp Asn
1               5                   10                  15
```

( 2 ) INFORMATION FOR SEQ ID NO:5:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: porcine ( x i ) SEQUENCE DESCRIPTION: SEQ ID NO:5:

```
Gly Gly Phe Leu Arg Arg Ile Arg Pro Lys Leu Lys Trp Asp
1               5                   10
```

( 2 ) INFORMATION FOR SEQ ID NO:6:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: porcine ( x i ) SEQUENCE DESCRIPTION: SEQ ID NO:6:

```
Gly Gly Phe Leu Arg Arg Ile Arg Pro Lys Leu Lys Trp
1               5                   10
```

( 2 ) INFORMATION FOR SEQ ID NO:7:

( i ) SEQUENCE CHARACTERISTICS:
      ( A ) LENGTH: 12 amino acids
      ( B ) TYPE: amino acid
      ( D ) TOPOLOGY: linear (i i) MOLECULE TYPE: protein (i i i) HYPOTHETICAL: NO (i v) ANTI-SENSE: NO (v i) ORIGINAL SOURCE:
  (A) ORGANISM: porcine (x i) SEQUENCE DESCRIPTION: SEQ ID NO:7:

```
Gly Gly Phe Leu Arg Arg Ile Arg Pro Lys Leu Lys
1               5                   10
```

(2) INFORMATION FOR SEQ ID NO:8:

(i) SEQUENCE CHARACTERISTICS:
    (A) LENGTH: 11 amino acids
    (B) TYPE: amino acid
    (D) TOPOLOGY: linear (i i) MOLECULE TYPE: protein (i i i) HYPOTHETICAL: NO (i v) ANTI-SENSE: NO (v i) ORIGINAL SOURCE:
    (A) ORGANISM: porcine (x i) SEQUENCE DESCRIPTION: SEQ ID NO:8:

```
Gly Gly Phe Leu Arg Arg Ile Arg Pro Lys Leu
1               5                   10
```

(2) INFORMATION FOR SEQ ID NO:9:

(i) SEQUENCE CHARACTERISTICS:
    (A) LENGTH: 10 amino acids
    (B) TYPE: amino acid
    (D) TOPOLOGY: linear (i i) MOLECULE TYPE: protein (i i i) HYPOTHETICAL: NO (i v) ANTI-SENSE: NO (v i) ORIGINAL SOURCE:
    (A) ORGANISM: porcine (x i) SEQUENCE DESCRIPTION: SEQ ID NO:9:

```
Gly Gly Phe Leu Arg Arg Ile Arg Pro Lys
1               5                   10
```

(2) INFORMATION FOR SEQ ID NO:10:

(i) SEQUENCE CHARACTERISTICS:
    (A) LENGTH: 9 amino acids
    (B) TYPE: amino acid
    (D) TOPOLOGY: linear (i i) MOLECULE TYPE: protein (i i i) HYPOTHETICAL: NO (i v) ANTI-SENSE: NO (v i) ORIGINAL SOURCE:
    (A) ORGANISM: porcine (x i) SEQUENCE DESCRIPTION: SEQ ID NO:10:

```
Gly Gly Phe Leu Arg Arg Ile Arg Pro
1               5
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: porcine ( x i ) SEQUENCE DESCRIPTION: SEQ ID NO:11:

```
Gly Gly Phe Leu Arg Arg Ile Arg
1               5
```

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: porcine ( x i ) SEQUENCE DESCRIPTION: SEQ ID NO:12:

```
Gly Gly Phe Leu Arg Arg Ile
1               5
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: porcine ( x i ) SEQUENCE DESCRIPTION: SEQ ID NO:13:

```
Gly Phe Leu Arg Arg Ile Arg Pro Lys Leu Lys Trp Asp Asn Gln
1               5                   10                  15
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO (v i) ORIGINAL SOURCE:
    (A) ORGANISM: porcine (x i) SEQUENCE DESCRIPTION: SEQ ID NO:14:

Gly Phe Leu Arg Arg Ile Arg Pro Lys Leu Lys Trp Asp Asn
1               5                   10

(2) INFORMATION FOR SEQ ID NO:15:

(i) SEQUENCE CHARACTERISTICS:
        (A) LENGTH: 13 amino acids
        (B) TYPE: amino acid
        (D) TOPOLOGY: linear (i i) MOLECULE TYPE: protein (i i i) HYPOTHETICAL: NO (i v) ANTI-SENSE: NO (v i) ORIGINAL SOURCE:
        (A) ORGANISM: porcine (x i) SEQUENCE DESCRIPTION: SEQ ID NO:15:

Gly Phe Leu Arg Arg Ile Arg Pro Lys Leu Lys Trp Asp
1               5                   10

(2) INFORMATION FOR SEQ ID NO:16:

(i) SEQUENCE CHARACTERISTICS:
        (A) LENGTH: 12 amino acids
        (B) TYPE: amino acid
        (D) TOPOLOGY: linear (i i) MOLECULE TYPE: protein (i i i) HYPOTHETICAL: NO (i v) ANTI-SENSE: NO (v i) ORIGINAL SOURCE:
        (A) ORGANISM: porcine (x i) SEQUENCE DESCRIPTION: SEQ ID NO:16:

Gly Phe Leu Arg Arg Ile Arg Pro Lys Leu Lys Trp
1               5                   10

(2) INFORMATION FOR SEQ ID NO:17:

(i) SEQUENCE CHARACTERISTICS:
        (A) LENGTH: 11 amino acids
        (B) TYPE: amino acid
        (D) TOPOLOGY: linear (i i) MOLECULE TYPE: protein (i i i) HYPOTHETICAL: NO (i v) ANTI-SENSE: NO (v i) ORIGINAL SOURCE:
        (A) ORGANISM: porcine (x i) SEQUENCE DESCRIPTION: SEQ ID NO:17:

Gly Phe Leu Arg Arg Ile Arg Pro Lys Leu Lys
1               5                   10

(2) INFORMATION FOR SEQ ID NO:18:

(i) SEQUENCE CHARACTERISTICS:
        (A) LENGTH: 10 amino acids ( B ) TYPE: amino acid
            ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
            ( A ) ORGANISM: porcine ( x i ) SEQUENCE DESCRIPTION: SEQ ID NO:18:

Gly Phe Leu Arg Arg Ile Arg Pro Lys Leu
    1               5                   10

( 2 ) INFORMATION FOR SEQ ID NO:19:

( i ) SEQUENCE CHARACTERISTICS:
            ( A ) LENGTH: 9 amino acids
            ( B ) TYPE: amino acid
            ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
            ( A ) ORGANISM: porcine ( x i ) SEQUENCE DESCRIPTION: SEQ ID NO:19:

Gly Phe Leu Arg Arg Ile Arg Pro Lys
    1               5

( 2 ) INFORMATION FOR SEQ ID NO:20:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
            ( A ) ORGANISM: porcine ( x i ) SEQUENCE DESCRIPTION: SEQ ID NO:20:

Gly Phe Leu Arg Arg Ile Arg Pro
    1               5

( 2 ) INFORMATION FOR SEQ ID NO:21:

( i ) SEQUENCE CHARACTERISTICS:
            ( A ) LENGTH: 7 amino acids
            ( B ) TYPE: amino acid
            ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
            ( A ) ORGANISM: porcine ( x i ) SEQUENCE DESCRIPTION: SEQ ID NO:21:

```
        Gly  Phe  Leu  Arg  Arg  Ile  Arg
        1                 5
```

( 2 ) INFORMATION FOR SEQ ID NO:22:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: porcine ( x i ) SEQUENCE DESCRIPTION: SEQ ID NO:22:

```
        Gly  Phe  Leu  Arg  Arg  Ile
        1                 5
```

( 2 ) INFORMATION FOR SEQ ID NO:23:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
      ( A ) ORGANISM: porcine ( x i ) SEQUENCE DESCRIPTION: SEQ ID NO:23:

```
   Gly  Gly  Phe  Leu  Arg  Arg  Ile  Arg  Pro  Lys  Leu  Lys  Trp  Asp  Asn  Gln
   1                  5                           10                          15
```